United States Patent [19]

Smith

[11] 4,117,233

[45] Sep. 26, 1978

[54] 2,2-DIFLUORO-13,14-DIDEHYDRO-11-DEOXY-17-PHENYL-18,19,20-TRINOR-PGF$_2\alpha$ COMPOUNDS

[75] Inventor: Herman W. Smith, Kalamazoo, Mich.

[73] Assignee: The Upjohn Company, Kalamazoo, Mich.

[21] Appl. No.: 821,007

[22] Filed: Aug. 1, 1977

Related U.S. Application Data

[62] Division of Ser. No. 657,740, Feb. 13, 1976.

[51] Int. Cl.$^2$ .......................................... C07C 177/00
[52] U.S. Cl. ....................................... 560/55; 560/60; 260/408; 260/410; 260/410.5; 260/410.9R; 260/413; 562/465
[58] Field of Search ............... 560/55, 60; 260/520 B, 260/520 R, 408, 410, 410.5, 410.9, 413

[56] References Cited

PUBLICATIONS

Derwent Abstract 4723U–B DT-2305044-Q Sep. 8, 1973.
Derwent Abstract 18176Y/11 BG 846-080 Oct. 3, 1977.
Derwent Abstract 61891X/33 DT 2603-172 May 8, 1976.
Derwent Abstract 59715X/32 BE 839-533 Jan. 7, 1976.
Derwent Abst. 79219X/42, U.S. 3984400 May 10, 1976.

*Primary Examiner*—Paul J. Killos
*Attorney, Agent, or Firm*—Robert A. Armitage

[57] ABSTRACT

This invention comprises certain analogs of the prostaglandins in which the double bond between C-13 and C-14 is replaced by a triple bond. Also provided in this invention, are novel chemical processes and novel chemical intermediates useful in the preparation of the above prostaglandin analogs. These prostaglandin analogs exhibit prostaglandin-like activity, and are accordingly useful for the same pharmacological purposes as the prostaglandins. Among these purposes are blood pressure lowering, labor induction at term, reproductive-cycle regulation, gastric antisecretory action, and the like.

73 Claims, No Drawings

2,2-DIFLUORO-13,14-DIDEHYDRO-11-DEOXY-17-PHENYL-18,19,20-TRINOR-PGF$_2\alpha$ COMPOUNDS The present application is a divisional application of Ser. No. 657,740, filed Feb. 13, 1976, now pending issuance as a U.S. Patent.

The present invention relates to prostaglandin analogs, for which the essential material constituting disclosure therefor is incorporated by reference here from Ser. No. 820,974, filed Aug. 1, 1977, which is a divisional application of Ser. No. 657,740.

I claim:

1. A prostaglandin analog of the formula

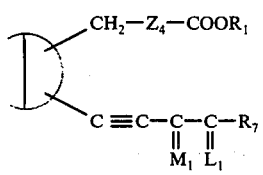

wherein D is

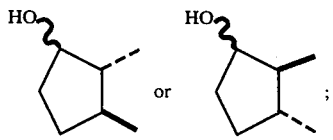

wherein $Z_4$ is cis-CH=CH—CH$_2$—(CH$_2$)$_g$—CF$_2$—, wherein g is one, 2, or 3;
wherein $R_7$ is

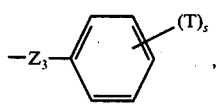

wherein $Z_3$ is oxa or methylene, s is zero, one, 2, or 3, and T is chloro, fluoro, trifluoromethyl, alkyl of one to 3 carbon atoms, inclusive, or alkoxy of one to 3 carbon atoms, inclusive, the various T's being the same or different, with the proviso that not more than two T's are other than alkyl;
wherein $L_1$ is

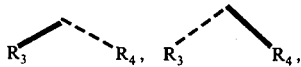

or a mixture of

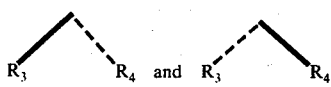

wherein $R_3$ and $R_4$ are hydrogen, methyl, or fluoro, being the same or different with the proviso that one of $R_3$ and $R_4$ is methyl only when the other is hydrogen or methyl, with the further proviso that one or both of $R_3$ and $R_4$ is fluoro only when $Z_3$ is methylene;
wherein $M_1$ is

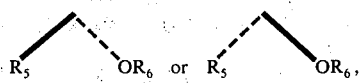

wherein $R_5$ and $R_6$ are hydrogen or methyl, with the proviso that one of $R_5$ and $R_6$ is methyl only when the other is hydrogen; and
wherein $R_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, phenyl substituted with one, two, or three chloro or alkyl of one to 3 carbon atoms, inclusive, or a pharmacologically acceptable cation.

2. A compound according to claim 1, wherein D is

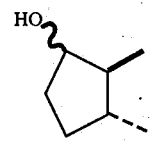

3. A compound according to claim 2, wherein $M_1$ is

4. A compound according to claim 3, wherein g is one.

5. A compound according to claim 4, wherein $R_3$, $R_4$, $R_5$, and $R_6$ are all hydrogen.

6. 15-epi-2,2-difluoro-13,14-didehydro-8$\beta$,12$\alpha$-11-deoxy-17-phenyl-18,19,20-trinor-PGF$_2\alpha$, methyl ester, a compound according to claim 4.

7. A compound according to claim 2, wherein $M_1$ is

8. A compound according to claim 7, wherein g is three.

9. A compound according to claim 7, wherein g is one.

10. A compound according to claim 9, wherein $R_3$ and $R_4$ are both hydrogen.

11. A compound according to claim 10, wherein $R_5$ is methyl.

12. 2,2-Difluoro-15-methyl-13,14-didehydro-8$\beta$,12$\alpha$-11-deoxy-17-phenyl-18,19,20-trinor-PGF$_2\alpha$, a compound according to claim 11.

13. 2,2-Difluoro-15-methyl-13,14-didehydro-8$\beta$,12$\alpha$-11-deoxy-17-phenyl-18,19,20-trinor-PGF$_2\alpha$, methyl ester, a compound according to claim 11.

14. A compound according to claim 10, wherein $R_6$ is methyl.

15. 2,2-Difluoro-13,14-didehydro-8$\beta$,12$\alpha$-11-deoxy-17-phenyl-18,19,20-trinor-PGF$_2\alpha$, 15-methyl ether, a compound according to claim 14.

16. 2,2-Difluoro-13,14-didehydro-8$\beta$,12$\alpha$-11-deoxy-17-phenyl-18,19,20-trinor-PGF$_2\alpha$, methyl ester, 15-methyl ether, a compound according to claim 14.

17. A compound according to claim 10, wherein $R_5$ and $R_6$ are both hydrogen.

18. 2,2-Difluoro-13,14-didehydro-8β,12α-11-deoxy-17-phenyl-18,19,20-trinor-PGF₂α, a compound according to claim 17.

19. 2,2-Difluoro-13,14-didehydro-8β,12α-11-deoxy-17-phenyl-18,19,20-trinor-PGF₂α, methyl ester, a compound according to claim 17.

20. A compound according to claim 9, wherein at least one of R₃ and R₄ is methyl.

21. A compound according to claim 20, wherein R₃ and R₄ are both methyl.

22. A compound according to claim 21, wherein R₅ is methyl.

23. 2,2-Difluoro-15,16,16-trimethyl-13,14-didehydro-8β,12α-11-deoxy-17-phenyl-18,19,20-trinor-PGF₂α, methyl ester, a compound according to claim 22.

24. A compound according to claim 21, wherein R₆ is methyl.

25. 2,2-Difluoro-16,16-dimethyl-13,14-didehydro-8β,12α-11-deoxy-17-phenyl-18,19,20-trinor-PGF₂α, methyl ester, 15-methyl ester, a compound according to claim 24.

26. A compound according to claim 21, wherein R₅ and R₆ are both hydrogen.

27. 2,2-Difluoro-16,16-dimethyl-13,14-didehydro-8β,12α-11-deoxy-17-phenyl-18,19,20-trinor-PGF₂α, a compound according to claim 26.

28. 2,2-Difluoro-16,16-dimethyl-13,14-didehydro-8β,12α-11-deoxy-17-phenyl-18,19,20-trinor-PGF₂α, methyl ester, a compound according to claim 26.

29. A compound according to claim 9, wherein at least one of R₃ and R₄ is fluoro.

30. A compound according to claim 29, wherein R₃ and R₄ are both fluoro.

31. A compound according to claim 30, wherein R₅ is methyl.

32. 2,2,16,16-Tetrafluoro-15-methyl-13,14-didehydro-8β,12α-11-deoxy-17-phenyl-18,19,20-trinor-PGF₂α, methyl ester, a compound according to claim 31.

33. A compound according to claim 30, wherein R₆ is methyl.

34. 2,2,16,16-Tetrafluoro-13,14-didehydro-8β,12α-11-deoxy-17-phenyl-18,19,20-trinor-PGF₂α, methyl ester, 15-methyl ether, a compound according to claim 33.

35. A compound according to claim 30, wherein R₅ and R₆ are both hydrogen.

36. 2,2,16,16-Tetrafluoro-13,14-didehydro-8β,12α-11-deoxy-17-phenyl-18,19,20-trinor-PGF₂α, a compound according to claim 35.

37. 2,2,16,16-Tetrafluoro-13,14-didehydro-8β,12α-11-deoxy-17-phenyl-18,19,20-trinor-PGF₂α, methyl ester, a compound according to claim 35.

38. A compound according to claim 1, wherein D is

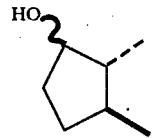

39. A compound according to claim 38, wherein M₁ is

40. A compound according to claim 39, wherein g is one.

41. A compound according to claim 40, wherein R₃, R₄, R₅, and R₆ are all hydrogen.

42. 15-epi-2,2-Difluoro-13,14-didehydro-11-deoxy-17-phenyl-18,19,20-trinor-PGF₂α, methyl ester, a compound according to claim 41.

43. A compound according to claim 38, wherein M₁ is

44. A compound according to claim 43, wherein g is three.

45. A compound according to claim 43, wherein g is one.

46. A compound according to claim 45, wherein R₃ and R₄ are both hydrogen.

47. A compound according to claim 46, wherein R₅ is methyl.

48. 2,2-Difluoro-15-methyl-13,14-didehydro-11-deoxy-17-phenyl-18,19,20-trinor-PGF₂α, a compound according to claim 47.

49. 2,2-Difluoro-15-methyl-13,14-didehydro-11-deoxy-17-phenyl-18,19,20-trinor-PGF₂α, methyl ester, a compound according to claim 47.

50. A compound according to claim 46, wherein R₆ is methyl.

51. 2,2-Difluoro-13,14-didehydro-11-deoxy-17-phenyl-18,19,20-trinor-PGF₂α, 15-methyl ether, a compound according to claim 50.

52. 2,2-Difluoro-13,14-didehydro-11-deoxy-17-phenyl-18,19,20-trinor-PGF₂α, methyl ester, 15-methyl ether, a compound according to claim 50.

53. A compound according to claim 46, wherein R₅ and R₆ are both hydrogen.

54. 2,2-Difluoro-13,14-didehydro-11-deoxy-17-phenyl-18,19,20-trinor-PGF₂α, a compound according to claim 50.

55. 2,2-Difluoro-13,14-didehydro-11-deoxy-17-phenyl-18,19,20-trinor-PGF₂α, methyl ester, a compound according to claim 53.

56. A compound according to claim 45, wherein at least one of R₃ and R₄ is methyl.

57. A compound according to claim 56, wherein R₃ and R₄ are both methyl.

58. A compound according to claim 57, wherein R₅ is methyl.

59. 2,2-Difluoro-15,16,16-trimethyl-13,14-didehydro-11-deoxy-17-phenyl-18,19,20-trinor-PGF₂α, methyl ester, a compound according to claim 58.

60. A compound according to claim 57, wherein R₆ is methyl.

61. 2,2-Difluoro-16,16-dimethyl-13,14-didehydro-11-deoxy-17-phenyl-18,19,20-trinor-PGF₂α, methyl ester, 15-methyl ether, a compound according to claim 60.

62. A compound according to claim 57, wherein R₅ and R₆ are both hydrogen.

63. 2,2-Difluoro-16,16-dimethyl-13,14-didehydro-11-deoxy-17-phenyl-18,19,20-trinor-PGF₂α, a compound according to claim 62.

64. 2,2-Difluoro-16,16-dimethyl-13,14-didehydro-11-deoxy-17-phenyl-18,19,20-trinor-PGF₂α, methyl ester, a compound according to claim 62.

65. A compound according to claim 45, wherein at least one of R₃ and R₄ is fluoro.

66. A compound according to claim 65, wherein $R_3$ and $R_4$ are both fluoro.

67. A compound according to claim 66, wherein $R_5$ is methyl.

68. 2,2,16,16-Tetrafluoro-15-methyl-13,14-didehydro-11-deoxy-17-phenyl-18,19,20-trinor-PGF$_2\alpha$, methyl ester, a compound according to claim 67.

69. A compound according to claim 66, wherein $R_6$ is methyl.

70. 2,2,16,16-Tetrafluoro-13,14-didehydro-11-deoxy-17-phenyl-18,19,20-trinor-PGF$_2\alpha$, methyl ester, 15-methyl ether, a compound according to claim 69.

71. A compound according to claim 66, wherein $R_5$ and $R_6$ are both hydrogen.

72. 2,2,16,16-Tetrafluoro-13,14-didehydro-11-deoxy-17-phenyl-18,19,20-trinor-PGF$_2\alpha$, a compound according to claim 71.

73. 2,2,16,16-Tetrafluoro-13,14-didehydro-11-deoxy-17-phenyl-18,19,20-trinor-PGF$_2\alpha$, methyl ester, a compound according to claim 71.

* * * * *

UNITED STATES PATENT OFFICE
CERTIFICATE OF CORRECTION

Patent No. 4,117,233      Dated September 26, 1978

Inventor(s) Herman W. Smith

It is certified that error appears in the above-identified patent and that said Letters Patent are hereby corrected as shown below:

Column 1, line 12, "filed August 1, 1977," should read -- filed August 1, 1977, now U.S. Patent 4,099,015, --

*Signed and Sealed this*

*Twenty-eighth* Day of *June 1983*

[SEAL]

Attest:

GERALD J. MOSSINGHOFF

*Attesting Officer*     *Commissioner of Patents and Trademarks*